United States Patent
Kolpashchikov et al.

(10) Patent No.: US 9,121,053 B2
(45) Date of Patent: Sep. 1, 2015

(54) METHOD OF DETECTING SINGLE NUCLEOTIDE POLYMORPHISMS

(75) Inventors: Dmitry Kolpashchikov, Winter Park, FL (US); John Katz, Sao Paulo (BR)

(73) Assignees: University of Central Florida Research Foundation, Inc., Orlando, FL (US); Scheme Lab, Ltda. (BR)

( * ) Notice: Subject to any disclaimer, the term of this patent is extended or adjusted under 35 U.S.C. 154(b) by 0 days.

(21) Appl. No.: 13/809,018

(22) PCT Filed: Jul. 8, 2011

(86) PCT No.: PCT/US2011/043389
§ 371 (c)(1),
(2), (4) Date: Apr. 29, 2013

(87) PCT Pub. No.: WO2012/006542
PCT Pub. Date: Jan. 12, 2012

(65) Prior Publication Data
US 2014/0072967 A1    Mar. 13, 2014

Related U.S. Application Data

(60) Provisional application No. 61/362,341, filed on Jul. 8, 2010.

(51) Int. Cl.
*C12Q 1/68* (2006.01)
*C12P 19/34* (2006.01)

(52) U.S. Cl.
CPC ............ *C12Q 1/6827* (2013.01); *C12Q 1/6858* (2013.01)

(58) Field of Classification Search
CPC .................................................... C12Q 1/6876
See application file for complete search history.

(56) References Cited

U.S. PATENT DOCUMENTS 7,282,328 B2 * 10/2007 Kong et al. .................. 435/6.12

OTHER PUBLICATIONS

Kolpashchikov, D.M. Split DNA enzyme for visual single nucleotide polymorphism typing. J. Am. Chem. Soc. (2008) 130:2934-2935.*
Tong et al. Development of isothermal TaqMan assays for detection of biothreat organisms. BioTechniques (2008) vol. 45, No. 5, pp. 543-557.*
PCT/US2011/043389; International Search Report and Written Opinion; Mar. 16, 2012.
Kolpashchikov, D.M. "A binary DNA probe for highly specific nucleic acid recognition", Journal of the American Chemical Society, 2006, vol. 128(32), pp. 10625-10628.
Detter, J.S. et al., "Isothermal strand-displacement amplification applications for high-throughput genomics", Genomics, 2002, vol. 80(6), pp. 691-698.
Papas, T.S. et al., "Presence of DNA polymerase in lymphosarcoma in northern pike", Cancer Research, 1977, vol. 37(9), pp. 3214-3217.
Kolpashchikov, D.M., "Binary malachite green aptamer for fluorescent detection of nucleic acids", Journal of the American Chemical Society, 2005, vol. 126(36), pp. 12442-12443.
Vincent, M. et al., "Helicase-dependent isothermal DNA amplification", EMBO Reports, 2004, vol. 5(8), pp. 795-800.

* cited by examiner

*Primary Examiner* — Kenneth R. Horlick
*Assistant Examiner* — David Thomas
(74) *Attorney, Agent, or Firm* — Timothy H. Van Dyke; Beusse, Wolter, Sanks & Maire, PLLC

(57) ABSTRACT

Use of low-temperature nucleic acid amplification and binary probes to detect sequences and single nucleotide polymorphisms.

16 Claims, No Drawings

SEQUENCE LISTING

<160> NUMBER OF SEQ ID NOS: 7

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1 gggcggttg gg                                                            12

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gggcgggatg gg                                                           12

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cagagaaaga caatatagtt cc                                                22

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aaatgcttgc tagaccaa                                                     18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tggagatcaa gggtaggg                                                     18

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gggttgggcg agcaaga                                                      17

```
<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tggaggtcaa gggtaggg                                                      18
```

METHOD OF DETECTING SINGLE NUCLEOTIDE POLYMORPHISMS

BACKGROUND OF THE INVENTION

Single nucleotide polymorphisms (SNPs) are DNA sequence variations that occur when a single nucleotide (A, T, C, or G) in the genome sequence is altered. For example, a SNP might change the DNA sequence AAGGCTAA to ATGGCTAA. For a variation to be considered a SNP, it generally—but not always—occurs in at least 1% of the population. SNPs make up ~90% of all human genetic variation, and occur every 100 to 300 bases along the 3-billion-base human genome. SNPs can occur in coding (gene) and noncoding regions of the genome. Many SNPs have no effect on cell function, but others have been associated with inherited traits, genetic diseases, age-associated diseases, and responses to drugs and environmental factors.

SNP genotyping assays are genetic tests that determine the presence of a sequence in nucleic acid, which can be used to detect the presence of SNPs —or other sequence variations in nucleic acids, e.g., microsattelites, deletions and insertions, duplications, and translocations. SNP genotyping assays can be separated into two groups based on mechanisms: (1) primer extension assays (including sequencing and PCR), and (2) hybridization assays (e.g., molecular beacons, microarrays, oligonucleotide ligation, and allele-specific endonuclease cleavage (e.g., invader assay)). Many assays require input of nucleic acid at quantities greater than typical yields of nucleic acid isolation procedures, and necessitate a nucleic acid amplification step to amplify nucleic acids in sufficient quantity to be detectable by the assay. The nucleic acid amplification steps use (1) sequence-specific primers to amplify regions of interest of nucleic acid (e.g. containing a SNP), and (2) high hybridization temperatures, necessary for sequence-specific primers to specifically hybridized and amplify template nucleic acid, which leads to specific amplification. In absence of high hybridization temperatures, the yield of amplified product drops and disappears from electrophoretic gels, and multiple background products appear (Henegariu, et. al., Biotechniques, 23:504 (1997)).

Nucleic acid amplification can be (1) thermocycling, e.g. PCR, using multiple heating cycles of 94° C., 55° C., and 72° C. for template denaturation, primer hybridization, and primer extension, respectively; or (2) isothermal, e.g., performed substantially at a single temperature, e.g. employing different mechanisms to bypass the denaturation step, and using single heating cycles of 37° C.-to-55° C. for primer hybridization and primer extension. Examples of isothermal amplification—capable of amplifying naturally occurring DNA or RNA—include Qβ replicase (Tyagi et al., PNAS USA 93:5395, 1996); self-sustained sequence replication, 3SR (Guatelli et al., PNAS USA 87:1874, 1990); strand displacement amplification, SDA (Walker et al., PNAS USA 89:392, 1992); and helicase dependent amplification (U.S. application Ser. No. 10/665,633). SNP genotyping assays requiring nucleic acid amplification—and its use of high hybridization temperatures—are not ideal for use in diagnostic assays, especially in kits and apparatuses in Point-of-Care (POC) settings and patient use. Towards fulfilling this need, a new combination of SNP genotyping assay and nucleic acid amplification was developed—whose nucleic acid amplification step can use heating cycles of less than 37° C., for example, room temperature.

SUMMARY OF THE INVENTION

The present invention describes a method and reagents for detecting sequences in nucleic acid, the method comprising (1) a nucleic acid amplification step, and (2) a SNP genotyping step. In some aspects, the sequences contain one or more single nucleotide polymorphisms (SNPs).

In some aspects, the disclosure provides a method of detecting sequences comprising (1) a nucleic acid amplification step that is substantially isothermal, and (2) a SNP genotyping step that uses one or more binary probes. In a preferred embodiment, the nucleic acid amplification uses specific primers and the isothermal temperature is room temperature. In some embodiments, the specific primers and/or binary probes are designed for room-temperature (e.g. 20-25° C.) hybridization, e.g., primers and/or analyte-binding arms with lengths from about 7 nucleotides to about 12 nucleotides. In other embodiments, the binary probe is a binary DNA peroxidase probe.

In some aspects, the disclosure provides a sequence-detecting kit comprising (1) one or more reagents needed for a nucleic acid amplification step, and (2) one or more reagents needed for a SNP genotyping step. In other aspects, the disclosure provides a sequence-detecting apparatus comprising (1) functionality for conducting a nucleic acid amplification step, and (2) a SNP genotyping step.

DETAILED DESCRIPTION OF THE INVENTION

Overview

The disclosure features a novel method and reagents for detecting sequences (e.g. SNPs or other sequence variations) in nucleic acid comprising (1) a nucleic acid amplification step, and (2) a SNP genotyping step. Described herein are kits and apparatuses designed for executing the nucleic acid amplification step and the SNP genotyping step.

It has been found that several colormetric SNP genotyping assays have template nucleic acid detection limits of 1 nM to 1 mM, corresponding to $6 \times 10^9$ to $6 \times 10^{12}$ molecules for a 10 μl reaction. This number of required molecules is greater than the number of molecules yielded from typical DNA harvests from saliva ($3 \times 10^7$ molecules ~110 μg gDNA/2 mLs) and blood ($1 \times 10^8$ molecules ~370 μg gDNA/10 mLs). To make SNP genotyping assays and colormetric SNP genotyping assays compatible with typical DNA harvest methods used in genetic testing, a step was developed involving a nucleic acid amplification step to amplify the template DNA. It was found that SNP genotyping assays—e.g. binary probes—can be used to detect sequences in nucleic acid that was specifically amplified—e.g. by using specific primers—under conditions of reduced primer specificity—e.g. low hybridization temperatures. The has been found that such use of specific primers and reduced specificity conditions provides (1) greater enrichment of the specific fragment containing the sequence or SNP than use of non-specific primers, and (2) greater convenience than use of high hybridization temperatures which require heating apparatuses (e.g. incubator or heater or thermal cycler).

It has also been found that for nucleic acids that are less heterogenous than human cell genomic DNA—e.g, genomic DNA from organisms with smaller genomes than humans (e.g. viruses); e.g., genomic DNA from human cells that has been fractionated—one can use specific primers that are shorter than those used in traditional nucleic acid amplification methods, e.g. primers less than 18 nucleotides, e.g. primers designed for room-temperature (e.g. 20-25° C.) hybridizations, e.g. primers from about 7 nucleotides to about 12 nucleotides. Also, it has been found that for analytes that are amplified nucleic acids (e.g. a specific fragment of nucleic acid amplified by at least 200-fold), one can use binary probes with analyte-binding arms that are shorter than those used in traditional SNP genotyping assays, e.g. arms designed for room-temperature (e.g. 20-25° C.) hybridizations, e.g. arms from about 7 nucleotides to about 12 nucleotides.

Thus, one unique feature of the present invention is use of a SNP genotyping assay in combination with nucleic acid amplification that optionally uses hybridization temperatures less than 37° C. As SNP genotyping assays can also be performed at room temperature, the present invention provides a generalized sequence or SNP detection method that can be performed at room temperature. The produced signal is a visually detectable color change. Together, these advantages make the method ideal for kits and apparatuses for POC diagnostics.

Nucleic Acid Amplification

In one embodiment, the nucleic acid amplification step involves the amplification (e.g. synthesis) of nucleic acid (or region thereof), also referred herein as template nucleic acid, by a RNA or DNA polymerase. In some aspects, the polymerase is mesophilic (e.g. *E. coli* DNA Polymerase I, Klenow Fragment, phi29 DNA Polymerase, T4 DNA Polymerase, Reverse Transcriptase). In other aspects, the polymerase is thermophilic (Taq) or psychrophilic (e.g. pike lymphosarcoma DNA polymerase (Papas et al., Cancer Research 37:3214 1977)), preferentially with activity at room-temperature (e.g. 20-25° C.).

In some aspects, the template nucleic acid is DNA or RNA. In other aspects, the template nucleic acid is naturally occurring or artificial. In some embodiments, the RNA is messenger RNA, ribosomal RNA, transfer RNA, small nuclear RNA, small nucleolar RNA, microRNA, or XIST RNA. In other embodiments, the DNA is genomic DNA (gDNA), episomal DNA, or mitochondrial DNA.

In some embodiments, the nucleic acid amplification step involves addition of other enzymes, for example, helicases, primases, and single-strand binding proteins, which can result in amplification of the template nucleic acid of at least 3-fold to greater than 1 million-fold.

In some embodiments, the nucleic acid amplification step includes other reagents to enhance amplification carried out by the RNA or DNA polymerase, or by other enzymes (e.g., helicases, primases, single-strand binding proteins). The reagents include one or more of nucleoside diphosphokinases, inorganic pyrophosphatases, an ATP regeneration system (e.g., combination of creatine kinase and phosphocreatine), a 5'-to-3' exonuclease (e.g., bacteriophage T7 gene 6 exonuclease), ligase (e.g., bacteriophage T7 DNA ligase), potassium glutamate, DMSO, and dextran polymer.

In some aspects, the nucleic acid amplification steps involve the addition of one or more oligonucleotide primers. Primers are utilized by polymerases to initiate DNA synthesis, are small nucleic acid molecules generally 18-to-30 bases in length, and are designed using known strategies (e.g., see Qiagen guidelines (Hilden, Germany), e.g. Qiagen News 5:1 1997). The primers can be DNA, RNA, or PNA, and are normally synthesized by chemical methods. The primers can also include nucleotide analogs or modified nucleotides (e.g. WIPO Standard ST.25 (2009), Appendix 2, WO 92/20823), e.g., having altered base or sugar, e.g., to substitute for a normal nucleotide in the primer or to impart a particular feature (e.g., increased stability or for detection). In other embodiments, the nucleic acid amplification step involves addition of reagents in place of, or addition to, the oligonucleotide primers, for example, primases and optionally helicases, for example, the gene 4 protein of bacteriophage T7, e.g., the 63-kDa T7 gene 4 protein that encodes the helicase/primase complex (Biohelix, Beverly, Mass.).

In some aspects, the primers are specific primers, which are complementary to certain regions of the template, and the region of the template that is amplified is defined by the primers utilized. In one embodiment, primer hybridization is performed at temperatures of 50° C.-to-65° C., e.g., 3-5° C. below the melting temperature of primers of 18-to-30 nucleotides. In a preferred embodiment, primer hybridization is performed at temperatures less than 37° C., more preferably at room temperature, and more preferably at 20-to-25° C. In another embodiment, the primers include random primers—a mixture of primers of many or all possible sequences, and all regions of the template are generally amplified by use of these primers (e.g. random hexamers)—e.g., use of random primers and one or more specific primers. In a preferred embodiment, the nucleic acid amplification is performed using isothermal conditions, i.e., heating cycle at (predominantly) one temperature, e.g. one temperature for primer hybridization and extension, e.g. 37° C.-to-65° C. Preferably the temperature for isothermal conditions is less than 37° C., more preferably the temperature is room temperature, and more preferably the temperature is 20-to-25° C.

In one embodiment, the nucleic acid amplification is a known nucleic acid amplification method performed using isothermal conditions; preferably the temperature for isothermal conditions is less than 37° C., more preferably the temperature is room temperature, and more preferably the temperature is 20-to-25° C. In a preferred embodiment, the known nucleic acid amplification method uses isothermal conditions and one or more specific primers (which are complementary to certain regions of the template, and the region of the template that is amplified is defined by the primer(s) utilized. Examples of known nucleic amplification methods include whole genome amplification (Lasken and Egholm, Trends in Biotech 21:531, 2003), for example, multiple displacement amplification (MDA) (using phi29 DNA polymerase) (Dean et al. PNAS 99:5261, 2002) and the pWGA platform (using the 63-kDa T7 gene 4 protein encoding a helicase/primase complex) of Biohelix (Beverly, Mass.). Other examples include Qβ replicase (Tyagi et al., PNAS USA 93:5395, 1996); self-sustained sequence replication, 3SR (Guatelli et al., PNAS USA 87:1874, 1990); strand displacement amplification, SDA (Walker et al., PNAS USA 89:392, 1992); and helicase dependent amplification, HDA (U.S. application Ser. No. 10/665,633).

In a preferred embodiment, the nucleic acid amplification using isothermal conditions amplifies a specific fragment of the template nucleic acid by use of specific primers and low hybridization temperature, e.g., less than 37° C., e.g., room temperature, e.g., 20-to-25° C. It has been found that nucleic acid amplification using low hybridization temperatures (25° C.) amplifies the specific fragment of template nucleic acid, e.g., by at least 200-fold.

In another embodiment, the nucleic acid amplification step is carried out in a solid matrix, such as agarose or polyacrylamide (Mitra and Church, Nucleic Acids Research 27:e34, 1999).

In some aspects, the enzymes of the nucleic acid amplification are treated—prior to inclusion in the reaction mixture—with UV irradiation to reduce the amplification of contaminating DNA in the enzyme preparations. Preferably the ultraviolet light dose is 10 to 1000 $\mu W/cm^2$ for 15 sec to 15 min.

Amplification of the template nucleic acid is such that the amount of amplified product is preferably at least about 3-fold amplified, more preferably the amplified product is 100-fold greater, or at least 1000-fold greater, or at least 10,000-fold greater, or at least 100,000-fold greater, or at least 1,000,000-fold greater, or at least 10,000,000-fold greater or even more than the DNA put into the reaction mixture.

In some aspects, the nucleic acid amplification step includes ATP and CTP in addition to the 4 dNTPs.

A preferred source of template nucleic acid to be amplified is lysed human cells and the template nucleic acid is gDNA. Preferably, the added gDNA template is 1 μg or less, and the reaction mixture is 10 to 200 μl. In some embodiments, the human cells are isolated from sources used in genetic testing, for example, buccal cells, blood, bone, ear (e.g. wax), hair (e.g. with root), nails, nasal secretion, saliva, sperm, skin, teeth, and tissue. In some embodiments, the human cells are fetal cells isolated from sources used in pre-natal genetic testing, for example, amniotic fluid, chorionic villus samples (CVS), direct fetal sample, maternal blood, placental tissue, and umbilical blood samples (PUBS). In some embodiments, the humans cells are cells of in vitro fertilization, for example, embryos (e.g. pre-implantation), eggs (e.g. oocytes and related cells), and sperm.

Other preferred sources of template nucleic acid to be amplified are organisms with genomes that are less heterogenous than human cells, e.g., organisms with genomes smaller than human cells (3200 million base pairs), e.g., organisms with genomes with less non-coding sequences (e.g. repeat sequences) than human cells. (Genome size and non-coding sequences increase sequence heterogeneity, and the probability of non-specific nucleic acid amplification). Examples of organisms with genomes smaller than human cells include insects (100 million-to-500 million base pairs), microbes (200,000-to-10 million base pairs), and viruses (5000-to-1 million base pairs).

In some embodiments, the nucleic acid amplification includes a prior template nucleic acid enrichment step (to reduce nucleic acid heterogeneity), where the template nucleic acid is positively selected, or other nucleic acid (e.g. contaminating) is negatively selected (and thereby enriches the specific template nucleic acid). For example, for amplification of the human Y chromosome, nucleic acids from human cells can be positively selected by use of Y chromosome antibodies to isolate Y chromosomes, or negatively enriched by use of antibodies against other (non-Y) chromosomes to deplete said chromosomes, and enrich for Y chromosomes. In other aspects, the nucleic acid amplification of template nucleic acid involves the addition of one or more oligonucleotide primers that are less than 18 nucleotides in length, e.g., primers with room temperature (e.g. 20-25° C.) hybridization temperatures, e.g., primers from about 7 nucleotides (e.g. poly G) to about 12 nucleotides (e.g. poly A) in length. In a preferred embodiment, the template nucleic acid (to be amplified) is less heterogenous than human cell genomic DNA, e.g., nucleic acid from (a) organisms with genomes smaller than human cells; (b) organisms with genomes with less non-coding sequences than human cells; or (c) human cells (e.g. genomic DNA) that have been subjected to prior template nucleic acid enrichment steps. For example, for viruses with 5000 base pair genomes, one can use primers of 8 nucleotides (which should hybridize to sequences randomly occurring at a frequency of 1:65,000 ($4^8$)); and for example, for viruses with 1 million base pair genomes, one can use primers of 12 nucleotides (which should hybridize to sequences randomly occurring at a frequency of 1:16 million ($4^{12}$)). Cells or viruses can be lysed to form a lysate, which is added to the nucleic acid amplification reaction mixture. Lysis can be carried out by any method known in the art, such as use of lysozyme or detergents.

The nucleic acid amplification step is generally carried out "in vitro", but can be adapted to be carried out in cells (in vivo) and tissues (in situ) using known methodologies. The nucleic acid amplification is performed using purified or at least substantially purified proteins.

SNP Genotyping

Nucleic acid to be genotype—e.g. contains the sequence or SNP to be detected—by SNP genotyping assays is also herein referred to as "analyte".

In one embodiment, the SNP genotyping step involves the detection of sequences or SNPs in analytes by a SNP genotyping assay. In a preferred embodiment, the SNP genotyping assay includes one or more binary probes. In some aspects, the analyte is template nucleic acid, e.g., DNA or RNA, naturally occurring or artificial, e.g., gDNA. In a preferred embodiment, the analyte is amplified nucleic acid from a nucleic acid amplification step.

Binary probes generally comprise two relatively short oligonucleotides (e.g. 7-10 nucleotides) that hybridize side-by-side to target sequences in the analyte, and generate a signal by different mechanisms (e.g., fluorescence, luminescence, or colormetric). The probes are called "binary" because the two parts of the probe act synergistically and the detection event occurs only when both parts are hybridized to the analyte. The two short oligonucleotides can be two separate molecules, or two parts of a single molecule.

In one aspect, the SNP genotyping step detects one or more sequences in nucleic acid (e.g. the analyte). In one embodiment, the SNP genotyping step is considered highly specific, and detects target sequences (one or more) and false positive sequences (one or more) at a ratio of 20:1 or greater. In another embodiment, the SNP genotyping step is considered moderately specific, and detects target sequences and false positive sequences at a ratio of <20:1 to >1:1.

In one embodiment, the SNP genotyping step detects one or more sequences (in nucleic acid) containing single nucleotide polymorphisms (e.g. that may or may not be present in a reference sequence, e.g. wildtype sequence). In a second embodiment, the SNP genotyping step detects one or more sequences containing single nucleotide mutations, additions, deletions, or substitutions (e.g. that may or may not be present in a reference sequence). In a third embodiment, the SNP genotyping step detects sequences containing larger polymorphisms, mutations, additions, deletions, duplications, and substitutions, for example, involving two, three, or more nucleotides. Mutations includes missense mutations, nonsense mutations, silent mutations, and splice-site mutations.

In some aspects, the binary probes are binary fluorimetric probes, e.g., two oligonucleotides hybridize to target sequences in the analyte to generate a fluorescent signal. In other aspects, the binary probes are binary luminescence probes, e.g., two oligonucleotides hybridize to target sequences to generate a luminescent signal. In other aspects, the binary probes are binary colormetric probes, e.g., two oligonucleotides hybridize to target sequences to generate a colormetric signal (e.g. visible color). Examples of binary probes include Xu et al., Nat. Biotech. 19:148, 2001; Sando et al., JACS 126:1081, 2004; Bichenkova et al., Biochem. Biophys. Res. Commun., 332:956, 2005; Kolpashchikov, JACS 127:12442, 2005; Kolpashchikov, JACS, 128:10625, 2006; Marti et al., J. Nucleic Acids Res., 34:3161, 2006; Kitamura et al., Anal. Biochem. 359:259, 2006; Kolpashchikov, ChemBioChem., 8:2039, 2007.

In a preferred embodiment, the binary probe is a binary colometric probe, e.g., a binary enzyme probe, e.g, a binary DNA peroxidase probe. (Kolpashchikov, JACS, 130:2934, 2008). In general, binary DNA peroxidase probes—upon binding target sequences in the analyte—form a guanine-quadruplex (G-quadruplex) that is capable of binding hemin.

G-quadruplex-bound hemin demonstrates hydrogen peroxidase-like activity that is ~250 times greater than free (unbound) hemin (Li et al., Biochem. 35:6911, 1996; Travascio et al., Chem. Biol. 5:505, 1998; Travascio et al., Chem. Biol. 6:779, 1999). The complex of binary DNA peroxidase probe and hemin can catalyze oxidation of various substrates to luminescent or colored products, which can be detected spectrophotometrically or visually (Xiao et al., JACS, 126; 7430, 2004; Li et al., Biosens Bioelectron 222:2570, 2007; Pavlov et al., Anal. Chem. 76:2152, 2004; Xiao et al., Chembiochem. 5:374-379, 2004).

In one embodiment, binary DNA peroxidase probe comprises two oligonucleotide strands, wherein, a first oligonucleotide strand comprises:
 a) an analyte binding arm at the 5'-terminus, which is complementary to and hybridizes to a first region of the analyte,
 b) an optional linker, and
 c) a porphyrin binding arm at the 3'-terminus,
and a second oligonucleotide strand comprises:
 a) a porphyrin binding arm at the 5'-terminus,
 b) an optional linker, and
 c) an analyte binding arm at the 3'-terminus, which is complementary to and hybridizes to a first region of the analyte.

The oligonucleotide strands can be DNA, RNA, PNA, LNA, or combination of thereof and can include nucleotide analogs or modified nucleotides (e.g. WIPO Standard ST.25 (2009), Appendix 2, WO 92/20823), e.g. having altered base or sugar. In a preferred embodiment, the porphyrin is hemin (trade name Panhematin), and the binding arms for hemin are DNA. In a second preferred embodiment, the binding arms for DNA analytes are DNA, for DNA-DNA duplexes are less stable than RNA-DNA duplexes, and therefore, more sensitive to nucleotide base pair mismatches, which improves their ability to detect SNPs.

In some aspects, the analyte- and porphyrin-binding arms are optionally connected to each other by linker molecules (which increase flexibility between the analyte- and hemin-binding arms of each probe strand permitting formation of a four-way junction with the analyte. The linker is not required if there is enough flexibility in the hemin- and analyte-binding arms of each strand to permit formation of the four-way junction with the analyte). In one embodiment, the linker is triethylene glycole. In another embodiment, the linker is an oligonucleotide linker.

The analyte-binding arms are customized for each particular analyte. In general, the arms are complementary to a target sequence (e.g. containing the SNP) on one strand of the template nucleic acid. For optimum selectivity, the analyte-binding arm of each strand of the probe can be 1000's of nucleotides in length. For binding of human genomic DNA analytes, analyte-binding arms are preferably 6-to-20 nucleotides, and more preferably about 10 nucleotides (which makes the total recognizable analyte fragment about 20 nucleotides, which will cover any unique sequence in the 3.2 billion nucleotide human genome (i.e., a 20 nucleotide sequence randomly occurs at a frequency of 1:1099 billion ($4^{20}$ nucleotides). For binding of analytes that are less heterogenous than human genomic DNA—for example, nucleic acids (a) from organisms with genomes smaller than human cells; (b) from organisms with genomes with less non-coding sequences than human cells; (c) subjected to prior template nucleic acid enrichment, and/or (d) amplified in nucleic acid amplification steps using one or more specific primers (e.g., a specific fragment of nucleic acid amplified by at least 200-fold)—the analyte-binding arms are designed for room-temperature (e.g. 20-25° C.) hybridization, e.g., the analyte-binding arms are from about 7 nucleotides to about 12 nucleotides.

In another aspect, for binding of analytes that are less heterogenous than human genomic DNA, the analyte-binding arm has a length that, with the second analyte-binding arm, permit the binary probe to hybridize to analytes at temperatures less than 37° C., more preferably room temperature, and more preferably between 20-to-25° C. Here, binary probe hybridization temperature, and the corresponding length (and sequence) of the analyte-binding arm, are determined experimentally using methods known in the art.

In some aspects, the analyte-binding arms have structure stabilization arms (SSA) for added sensitivity—which are additional nucleotide sequences (up to 40, preferably 3-10) added to the free end of the analyte binding arms that are complementary to and hybridize with an internal region of the analyte-binding arm to form a stem-loop structure.

In some aspects, the binary DNA peroxidase probe hybridizes to an analyte, enabling its G-quadruplex to noncovalently bind hemin by way of stacking and hydrophobic interactions, to form an enzyme-like molecule with hydrogen peroxidase-like activity. In other aspects, a more sensitive binary DNA peroxidase probe with a G-quadruplex covalently bound to hemin (via one or both of the antiparallel oligonucleotides), hybridizes to an analyte to form an enzyme-like molecule with hydrogen peroxidase-like activity.

The hemin-binding arms of the G-quadruplex can have different configurations. For example, the first hemin-binding arm can comprise 5'-gggttggg-3' and the second hemin-binding can comprise 3'-gggatggg-5'; the first binding arm can comprise 5'-gggcgggttggg-3' (SEQ ID NO. 1) and the second binding arm 3'-ggg-5'; the first binding arm 5'-ggg-3' and the second binding arm 3'-gggcgggatggg-5'(SEQ ID G. 2).

In some embodiments, the binary probe can be conjugated to one or more solid supports, e.g., gold nanoparticles. For example, the binary probes can be fixed to the surface of different gold nanoparticles, and on addition of template DNA, a polymer network forms, which can be detected, e.g., red-to-purple color change (Mirkin et al., Chem. Rev. 105: 1547, 2005; Sato, Anal. Sci., 23:17 2007; Murphy, The Analyst 129:970 2004).

The SNP genotyping step is generally carried out "in vitro", but can be adapted to be carried out in cells (in vivo) and tissues (in situ) using known methodologies.

Genetic Testing

In some aspects, the disclosure provides a method of detecting sequences or SNPs in humans cells. In other aspects, the disclosure provides a method of detecting sequences or SNPs in other eukaryotic cells (e.g., non-human mammalian cells, plant cells), viruses, and microbial cells (e.g., bacterial, yeast). In some embodiments, the method is used to detect sequences or SNPs associated with pathogenecity and drug resistance (e.g. rRNA mutations associated with antibiotic resistance in bacteria). In other embodiments, the method is used to detect sequences or SNPs associated with specific industrial and agriculture applications (e.g. mutations associated with a desired genetic modified organism (GMO) for a particular use, e.g., GMO crop planting).

In another embodiment, the invention features a method of detecting contaminating DNA by detecting the sequences or SNPs of the contaminating DNA. Contaminating DNA refers to any DNA that may be contaminating a preparation, for example, the DNA of an organism used to derived the preparation, or the DNA of a contaminating organism (e.g acquired during the making of the preparation).

In some aspects, the DNA is added to a first reaction mixture for the nucleic acid amplification step, and after adequate amplification for detection, part or all of the first reaction mixture is added to a second reaction mixture for the SNP genotyping step. In some embodiments, the first reaction mixture is added to the second reaction mixture before completion (e.g. adequate amplification) where the nucleic acid amplification step continues to completion during the SNP genotyping step. In other embodiments, the DNA is added to a combination of first reaction mixture and second reaction mixture, where the nucleic acid amplification step and SNP genotyping step can occur simultaneously, and optionally report the amount of amplified DNA containing the sequence or SNP in real time, e.g, real-time PCR (Gibson et al., Genome Research 6:995, 1996).

In another aspect, the invention features a kit for detecting sequences or SNPs. The kit can be a point-of-care (POC) kit. The kit preferably includes components for performing a nucleic acid amplification step and a SNP genotyping step. In one embodiment, the nucleic acid amplification is carried out in a first reaction mixture, and the SNP genotyping step is carried out in a second reaction mixture. In a preferred embodiment, the first reaction mixture includes reagents needed for nucleic acid amplification under isothermal conditions, and the second reaction mixture includes one or more binary probes. Alternatively, the nucleic acid amplification and SNP gentotyping are carried out in a single reaction mixture, e.g., a combination of the first and second reaction mixtures.

In another aspect, the invention features an apparatus for detecting sequences or SNPs. The apparatus can be a diagnostic or a POC diagnostic. The apparatus preferably involves a nucleic acid amplification step and a SNP genotyping step. In one embodiment, the nucleic acid amplification is carried out in a first reaction mixture, and the SNP genotyping step is carried out in a second reaction mixture. In a preferred embodiment, the first reaction mixture includes reagents needed for nucleic acid amplification under isothermal conditions, and the second reaction mixture includes one or more binary probes. Alternatively, the nucleic acid amplification and SNP gentotyping are carried out in a single reaction mixture, e.g., a combination of the first and second reaction mixtures.

The kit or apparatus, for example, can be provided which are configured to assist in executing the following steps:
1) Providing a template nucleic acid to a first reaction mixture comprising reagents needed for isothermal nucleic acid amplification.
2) Incubating the reaction mixture at room temperature for X min.
3) Transferring part or all of the first reaction mixture to a second reaction mixture comprising binary DNA peroxidase probe, hemin, peroxidase substrate, and other reagents needed for SNP genotyping.
4) Incubating the reaction mixture at room temperature for Y min.
5) Determining if the sequence or SNP is present by chemiluminescence or visible detection of the second reaction mixture.

In one embodiment, the peroxidase substrate is luminal for chemiluminescence detection. In a preferred embodiment, the peroxidase substrate is DAB (3-3'-diaminobenzidine tetrahydrochloride) or ABTS (2,2'-azino-bis(3-ethylbenzthiazoline-6-sulphonic acid) or TMB (3,3',5,5'-tetramethylbenzidine) for visual detection.

Other features and advantages of the invention will be apparent from the following description of the preferred embodiments thereof and from the claims. Citations in this application are hereby incorporated by reference, in their entirety.

Example 1

DNA Samples

Cheek swabs from 10 normal patients; 1 cystic fibrosis patient homozygous for the G551D mutation (1652G>A) in the CFTR gene; and 1 cystic fibrosis patient homozygous for the R553X mutation (1657C>T) in the CFTR gene are taken with an Easy-Swab and harvested using the BuccalQuick kit (TrimGen, Sparks, Md.). Briefly, the swab is washed in BuccalQuick kit Extraction Buffer, and the resulting DNA-containing buffer is vortexed, heated at 55° C. for 5 minutes and 90° C. for 3 minutes. The yield of the DNA is 1-to-2 µg per swab.

Primers

For nucleic acid amplification of DNA from normal and cystic fibrosis patients, two sets of primers are used: (1) forward primer [5'-CAG AGA AAG ACA ATA TAG TTC C-3', SEQ ID NO. 3] and reverse primer [5'-AAA TGC TTG CTA GAC CAA T-3', SEQ ID NO. 4] for amplification of a 114bp fragment of the CFTR gene (de Araûjo, Braz J Med Biol Res 38(1), 2005) and (2) random hexamer primers.

Binary Probes

For a binary DNA peroxidase probe specific for the G551 D mutation (1652G>A) of the CFTR gene, two oligonucleotide strands are used: (1) 5'-1652 strand, of sequence [5'-TGG AGA TCA AGG GTA GGG-3', SEQ ID NO. 5] containing an 5'-analyte binding arm (10 nucleotides) and 3'-hemin binding arm; and (2) 3'-WT strand, of sequence [5'-GGG TTG GGC GAG CAA GA-3', SEQ ID NO. 6] containing a 5'-hemin binding arm and 3'-analyte binding arm (9 nucleotides). For a binary DNA peroxidase probe specific for the corresponding wildtype sequence of the CFTR gene, two oligonucleotide strands are used: (1) 5'-WT strand, of sequence [5'-TGG AGG TCA AGG GTA GGG-3', SEQ ID NO. 7] containing an analyte binding arm (first 10 5'-nucleotides) and hemin binding arm; and (2) 3'-WT strand.

The two analyte binding arms of each oligonucleotide strand are selected with melting temperatures of 25-30° C., where the SNP of interest binds the middle of one analyte binding arm (e.g., compare sequence 5'-1652 and 5'-WT), and a SNP mismatch greatly reduces the melting temperature, resulting in probe unable to bind and assemble into an active form. For example, the melting temperature of strands 5'-1652 and 3'-WT—with analyte DNA from cystic fibrosis patients with the G551D mutation—is 25.0° C. and 27.3° C. respectively—calculated using OligoAnalyzer 3.1 (Integrated DNA Tecnologies, Coralville, Iowa), suitable for room-temperature hybridization. The melting temperature of the same strands, 5'-1652 and 3'-WT, with analyte DNA from normal patients with wild-type SNP is 2.4° C. and 27.3° C. respectively, the former not suitable for room-temperature hybridization, or probe assembly into an active form.

The two hemin binding arms of each oligonucleotide strand are selected following Kolpashchikov, JACS 130:2934, 2008.

A binary DNA peroxidase probe with oligonucleotide strands 5'-1652 and 3'-WT can be used to screen analyte DNA—and patients—for the G551D mutation of the CFTR gene, which is associated with cystic fibrosis. A positive signal, for example, a color reaction resulting from peroxidase-like activity, would indicate one chromosomal copy (heterozygote) or two chromosomal copies (homozygote) of the mutant SNP sequence; and no color reaction would indicate two chromosomal copies of normal, wildtype SNP sequence. Using a second binary DNA peroxidase probe with oligonucleotide strands 5'-WT and 3'-WT can distinguish heterozygotes and homozygotes for the mutant SNP sequence, where heterozygotes would give a positive signal stemming from their one chromosomal copy of wildtype SNP sequence, and homozygotes lacking wildtype SNP sequence would give a negative (no) signal.

In the example, other binary DNA peroxidase probes specific for other SNPs—from the CFTR gene or other genes—can be added to the same reaction to simultaneously (or sequentially) to detect other SNPs in a multiplex-type assay.

Reagents

Oligonucleotides are custom-made by Integrated DNA Technologies, Inc. (Coralville, Iowa). Hydrogen peroxide, 3-3'-diaminobenzidine tetrahydrochloride (DAB), 2,2'-azino-bis(3-ethylbenzthiazoline-6-sulphonic acid) (ABTS), hemin, and HEPES are from Sigma-Aldrich (St. Louis, Mo., USA).

Example 2

DNA Amplification

Two types of isothermal nucleic acid amplification steps are performed: (1) phi29 DNA polymerase (adapted from Dean et al. PNAS 99:5261, 2002); and (2) IsoAmpII Universal tHDA Kit (using helicase) of Biohelix (Beverly, Mass.).

A total of 12 samples of DNA—10 from normal patients, 1 from cystic fibrosis patient homozygous for the G551D mutation, and 1 cystic fibrosis patient homozygous for the R553X mutation—are amplified with each type of nucleic acid amplification.

For amplification using phi29 DNA polymerase, 200 ng of genomic DNA is added to a tube containing 37 mM Tris-HCl (pH 7.5), 50 mM KCl, 10 mM $MgCl_2$, 5 mM $(NH_4)_2SO_4$, 1 mM dNTPs, 50 pm forward primer, 50 pm reverse primer, 1 U/ml yeast pyrophosphatase, and 800 U/ml phi29 DNA polymerase, and the tube is incubated at 25° C. for 1 hour. For random primer amplification, hexamer primers (final [30 μM]) substitute forward and reverse primers.

For amplification using tHDA and helicase, 200 ng of genomic DNA is added to a tube containing 1× Annealing Buffer, 4 mM $MgSO_4$, 50 mM NaCl, 50 pm forward primer, 50 pm reverse primer, IsoAmp dNTP, and IsoAmp Enzyme Mix (as recommended by manufacturer), and the tube is incubate at 25° C. for 1 hour. For random primer amplification, hexamer primers (final [30 μM]) substitute forward and reverse primers.

Example 3

SNP Genotyping and Colormetric Assay

For genotyping patient DNA ("the analyte"), ½ of the nucleic acid amplification reaction is added to a tube containing 1 μM binary probes (with strands 5'-1652 and 3'-WT, or strands 5'-WI and 3'-WT), 50 mM HEPES pH 7.4, 50 mM $MgCl_2$, 20 mM KCl, 120 mM NaCl, 0.03% Triton X-100, 1% DMSO, hemin (125 nM), 1 mM $H_2O_2$, and 1 mM DAB. Duplicate samples are prepared without addition of binary probes (negative control). The tubes are incubated for 30 minutes at 25° C., then the tubes are photographed using an Olympus FE-170 digital camera (6 mega pixels).

After 30 minutes, samples from normal patients amplified with specific primers and detected with the 5'-WT/3'-WT binary probe are brown in color, as are samples from cystic fibrosis patients (with the G551D mutation) that are amplified with specific primers and detected with the 5'-1652/3'-WT binary probe. Negative controls, including samples of normal patients detected with 5'-1652/3'-WT probe, and cystic fibrosis patients detected with the 5'-WT/3'-WT probe, are almost clear in color.

Repeat genetic tests are performed using the same DNA amplification and SNP genotyping methodology, except the 1 mM DAB (whose product is brown in color) in the SNP genotyping step was substituted with 1 mM ABTS (whose product is green in color).

While various disclosed embodiments have been described above, it should be understood that they have been presented by way of example only, and not limitation. Numerous changes to the subject matter disclosed herein can be made in accordance with this Disclosure without departing from the spirit or scope of this Disclosure. In addition, while a particular feature may have been disclosed with respect to only one of several implementations, such feature may be combined with one or more other features of the other implementations as may be desired and advantageous for any given or particular application.

Thus, the breadth and scope of the subject matter provided in this Disclosure should not be limited by any of the above explicitly described embodiments. Rather, the scope of this Disclosure should be defined in accordance with the following claims and their equivalents.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The teachings of any patents, patent applications, technical or scientific articles or other references are incorporated herein in their entirety to the extent not inconsistent with the teachings herein.

What is claimed is:

1. A method of detecting a sequence in a region of nucleic acid, comprising:
   i. amplifying the region of nucleic acid comprising said sequence using at least one oligonucleotide primer, and a primer hybridization temperature of less than 37° C., wherein the amplifying is conducted without helicase; and
   ii. detecting said sequence in the amplified region of nucleic acid using at least one binary probe, wherein said binary probe comprises two separate oligonucleotide molecules each comprising a strand of 6-20 nucleotides that hybridize side by side to said sequence and when bound to said sequence interact to produce a detectable signal.

2. The method of claim 1, wherein the sequence is 1-to-12 nucleotides in length.

3. The method of claim 2, wherein the sequence is 1 nucleotide in length.

4. The method of claim 3, wherein the sequence is a single nucleotide polymorphism.

5. The method of claim 1, wherein the nucleic acid is RNA.

6. The method of claim 5, wherein the RNA is ribosomal RNA.

7. The method of claim 1, wherein the nucleic acid is DNA.

8. The method of claim 7, wherein the DNA is genomic DNA.

9. The method of claim 1, wherein the primer hybridization temperature is 20° C.-to-25° C.

10. The method of claim 1, wherein the amplification of nucleic acid uses mesophilic or psychrophilic DNA polymerases.

11. The method of claim 10, wherein the mesophilic DNA polymerase is phi29 DNA polymerase.

12. The method of claim 10, wherein the psychrophilic DNA polymerase is pike lymphosarcoma DNA polymerase.

13. The method of claim 1, wherein the binary probe is a binary fluorimetric probe, a binary luminescence probe, or a binary colormetric probe.

14. The method of claim 13, wherein the binary probe is a binary colormetric probe.

15. The method of claim 13, wherein the binary probe is a binary DNA peroxidase probe.

16. The method of claim 15, wherein the binary DNA peroxidase probe comprises a first and second oligonucleotide strand, wherein the first oligonucleotide strand comprises:
   a) an analyte binding arm at the 5'-terminus, which is complementary to and hybridizes to a first region of the analyte,
   b) an optional linker, and
   c) a porphyrin binding arm at the 3'-terminus, and the second oligonucleotide strand comprises:
   a) a porphyrin binding arm at the 5'-terminus,
   b) an optional linker, and
   c) an analyte binding arm at the 3'-terminus, which is complementary to and hybridizes to a first region of the analyte.

* * * * *